United States Patent
Kozup et al.

(10) Patent No.: US 8,586,811 B2
(45) Date of Patent: Nov. 19, 2013

(54) PROCESSES AND HYDROCARBON PROCESSING APPARATUSES FOR PREPARING MONO-OLEFINS

(75) Inventors: Steven C. Kozup, Chicago, IL (US); Joseph Edward Zimmermann, Arlington Heights, IL (US)

(73) Assignee: UOP LLC, Des Plaines, IL (US)

( * ) Notice: Subject to any disclaimer, the term of this patent is extended or adjusted under 35 U.S.C. 154(b) by 41 days.

(21) Appl. No.: 13/399,796

(22) Filed: Feb. 17, 2012

(65) Prior Publication Data

US 2013/0217933 A1    Aug. 22, 2013

(51) Int. Cl.
*C07C 5/08* (2006.01)
*C07C 5/03* (2006.01)
*C07C 5/327* (2006.01)

(52) U.S. Cl.
USPC ............ 585/324; 585/259; 585/654; 585/655

(58) Field of Classification Search
USPC .................... 585/324, 259, 654, 655
See application file for complete search history.

(56) References Cited

U.S. PATENT DOCUMENTS

| | | | |
|---|---|---|---|
| 4,761,509 A * | 8/1988 | Vora et al. ..................... 585/254 |
| 4,774,375 A | 9/1988 | Hammershaimb et al. |
| 5,220,097 A | 6/1993 | Lam et al. |
| 7,268,265 B1 | 9/2007 | Stewart et al. |
| 8,025,857 B2 | 9/2011 | Gartside et al. |
| 2009/0312591 A1 | 12/2009 | Schubert et al. |
| 2010/0145120 A1 | 6/2010 | Bouvart et al. |
| 2011/0245559 A1 | 10/2011 | da Silva Ferreira Alves et al. |

* cited by examiner

*Primary Examiner* — Thuan D Dang
(74) *Attorney, Agent, or Firm* — Arthur E. Gooding

(57) ABSTRACT

Processes and hydrocarbon processing apparatuses for preparing mono-olefins are provided. An exemplary process includes separating a hydrocarbon feed into a first fraction of carbon-containing compounds having less than or equal to 5 carbon atoms and a second fraction of compounds that have a lower vapor pressure than those in the first fraction. Dienes and/or acetylenes from the first fraction are selectively hydrogenated into corresponding mono-olefins. Paraffins from the first fraction are converted into corresponding mono-olefins. The converted mono-olefins are contact cooled with an impurity-containing liquid hydrocarbon stream, with the impurities in the impurity-containing liquid hydrocarbon stream having a lower vapor pressure than compounds in the first fraction. The dienes and/or acetylenes from the first fraction are selectively hydrogenated prior to converting the paraffins from the first fraction into mono-olefins and after separating the first fraction from the hydrocarbon feed.

8 Claims, 1 Drawing Sheet

PROCESSES AND HYDROCARBON PROCESSING APPARATUSES FOR PREPARING MONO-OLEFINS

TECHNICAL FIELD

The present invention generally relates to processes and hydrocarbon processing apparatuses for preparing mono-olefins, and more particularly relates to processes and hydrocarbon processing apparatuses for converting paraffins in a hydrocarbon feed into mono-olefins.

BACKGROUND

Light mono-olefins, such as ethylene, propylene, and butylene, serve as feeds for the production of numerous chemicals including hydrocarbon-based polymers such as polyethylene, polypropylene, and the like. Light mono-olefins are generally prepared from a hydrocarbon feed, which may be derived from petroleum or renewable feedstocks. Hydrocarbon feeds generally include a mixture of paraffins and other hydrocarbons such as dienes, acetylenes, and the like, as well as various impurities such as sulfur-, mercury-, arsenic-, nitrogen-, and/or oxygen-containing compounds.

Processes for preparing mono-olefins from hydrocarbon feed are well known in the art and generally involve a combination of separation steps and reaction steps to optimize yield of desired mono-olefins. In particular, processes for preparing mono-olefins generally involve separating the hydrocarbon feed in one or more fractionation columns, thereby separating fractions of higher vapor pressure from fractions of lower vapor pressure, with progressive fractions being separated, from those having higher vapor pressures to those having lower vapor pressures, in successive fractionation columns that operate in series. The separated fractions are then subject to cracking or dehydrogenation reactions, depending upon the content of the feed and particular process design, to yield mono-olefins. The cracking and dehydrogenation reactions also produce dienes and/or acetylenes which, if recycled back to the cracking or dehydrogenation reactions in a recycle stream, may result in deposition of coke upon conversion catalysts, such as dehydrogenation catalysts, used in the cracking and dehydrogenation reactions. Deposition of coke on the conversion catalysts used in the cracking and dehydrogenation reactions is undesirable and, therefore, the separated fractions are generally subject to a selective hydrogenation reaction to convert dienes and/or acetylenes from the separated fraction into corresponding mono-olefins after the cracking or dehydrogenation reactions.

After the separated fractions are subject to cracking or dehydrogenation reactions and selective hydrogenation, mono-olefins are then separated therefrom, with unreacted paraffins and other components recycled back to the fractionation columns. To separate the mono-olefins, the product stream to be separated must be in liquid form. However, the cracking and dehydrogenation reactions occur under harsh conditions, with the product stream generally in vapor form. As such, the product stream from the cracking or dehydrogenation reactions requires cooling and condensation prior to separation of the mono-olefins.

Various apparatuses and devices are known for cooling and condensing vaporized product streams from the cracking or dehydrogenation reactions. Air and water-cooled apparatuses are generally employed to cool the vaporized product streams prior to compressing the vaporized product streams in a compressor. Such air and water-cooled apparatuses generally exhibit a pressure drop of about 27.5 kilopascals (kPa) across the air and water-cooled apparatuses, thereby requiring the cracking or dehydrogenation reaction to occur at pressures of about 35.5 kPa to maintain flow of the vaporized product streams through the air and water-cooled apparatuses and into the compressor.

The vaporized product stream is then compressed to sufficiently high pressures (generally in the range of from 700 to 1400 kPa-g (100-200 psig)) to allow for cooling and condensation using air or water cooling after compressing. In order to minimize the energy associated with compression of the vaporized product stream, it is common to cool the vaporized product stream to about 38° C. using air or water cooled exchangers before entering the compressor. However, the associated pressure drop of the vaporized product stream through such air or water cooled exchangers, typically from 10 to 20 kPa, forces the cracking or dehydrogenation reaction to occur at higher pressures, which are not as favorable for the reactions. In particular, lower reaction pressures are generally desired for cracking and dehydrogenation reactions, with higher paraffin to olefin conversion obtainable due to favorable dehydrogenation equilibriums at lower pressures.

In an industrialized setting, it may be desirable to employ contact cooling to cool the vaporized product streams with a cool impurity-containing liquid hydrocarbon stream, such as a light cycle oil stream, after the cracking or dehydrogenation reactions due to ready availability of such cool impurity-containing liquid hydrocarbon streams. Contact cooling may be desirable due to low pressure drop of about 3.5 kPa that is generally attendant across the contact cooling apparatuses, thereby enabling the cracking and hydrogenation reactions to occur at lower pressures that enable maximized paraffin to olefin conversion to be attained. However, selective hydrogenation catalysts that include noble metals are sensitive to many impurities that are prevalent in the impurity-containing liquid hydrocarbon streams, such as light cycle oil, and may experience deactivation or reversible inhibition that requires catalyst recovery when exposed to such impurities. As such, contact cooling of the vaporized product streams using a cool liquid hydrocarbon stream is often unfeasible or requires non-traditional selective hydrogenation catalysts, which are free from noble metals, to be employed in the selective hydrogenation reaction.

Accordingly, it is desirable to provide processes for preparing mono-olefins that enable contact cooling using an impurity-containing liquid hydrocarbon stream to be employed in conjunction with selective hydrogenation of dienes and/or acetylenes, even while employing selective hydrogenation catalysts that include noble metals. It is also desirable to provide apparatuses configured to support processes for preparing mono-olefins that include a selective hydrogenation stage and a contact cooling stage in which an impurity-containing liquid hydrocarbon stream can be employed in the contact cooling stage with minimal effect on selective hydrogenation catalysts, even when the selective hydrogenation catalysts including noble metals are employed. Furthermore, other desirable features and characteristics of the present invention will become apparent from the subsequent detailed description of the invention and the appended claims, taken in conjunction with the accompanying drawings and this background of the invention.

BRIEF SUMMARY

Processes and hydrocarbon processing apparatuses for preparing mono-olefins are provided. In an embodiment, a process includes separating a hydrocarbon feed into a first fraction of carbon-containing compounds having less than or equal to 5 carbon atoms and a second fraction of compounds that have a lower vapor pressure than those in the first fraction. Dienes and/or acetylenes from the first fraction are selectively hydrogenated into corresponding mono-olefins. Paraffins from the first fraction are converted into corresponding mono-olefins in a conversion stream. The mono-olefins from the conversion stream are contact cooled with an impurity-containing liquid hydrocarbon stream, with the impurities in the impurity-containing liquid hydrocarbon stream having a lower vapor pressure than compounds in the first fraction. The dienes and/or acetylenes from the first fraction are selectively hydrogenated prior to converting the paraffins from the first fraction into mono-olefins and after separating the first fraction from the hydrocarbon feed.

In another embodiment, a process for preparing mono-olefins in a hydrocarbon processing apparatus is provided. The method includes separating a hydrocarbon feed into a first fraction of carbon-containing compounds having less than or equal to 5 carbon atoms and a second fraction of compounds that have a lower vapor pressure than those in the first fraction in a fractionation stage of the hydrocarbon processing apparatus. Dienes and/or acetylenes from the first fraction are selectively hydrogenated into corresponding mono-olefins within a selective hydrogenation stage of the hydrocarbon processing apparatus. Paraffins from the first fraction are converted into corresponding mono-olefins in a conversion stream within a conversion stage of the hydrocarbon processing apparatus. The mono-olefins from the conversion stream are contact cooled with an impurity-containing liquid hydrocarbon stream in a contact cooling stage of the hydrocarbon processing apparatus, with the impurities in the impurity-containing liquid hydrocarbon steam having a lower vapor pressure than compounds in the first fraction. The conversion stream is separated into a mono-olefin fraction and a paraffin-containing fraction in a mono-olefin separation stage after contact cooling the mono-olefins from the conversion stream. The paraffin-containing fraction comprises impurities from the impurity-containing liquid hydrocarbon stream, and the paraffin-containing fraction is recycled to the step of separating the hydrocarbon feed in the fractionation stage. The dienes and/or acetylenes from the first fraction are selectively hydrogenated prior to converting the paraffins from the first fraction into mono-olefins and after separating the first fraction from the hydrocarbon feed.

In another embodiment, a hydrocarbon processing apparatus for preparing mono-olefins is provided. The apparatus includes a fractionation stage for receiving the hydrocarbon feed and separating the hydrocarbon feed into a plurality of fractions. A selective hydrogenation stage is in fluid communication with the fractionation stage for receiving a fraction from the fractionation stage and selectively hydrogenating dienes and/or acetylenes in the fraction into corresponding mono-olefins. A conversion stage is in fluid communication with the selective hydrogenation stage for receiving effluent produced from selectively hydrogenating the dienes and/or acetylenes and for converting paraffins in the effluent into corresponding mono-olefins in a conversion stream. A contact cooling stage is in fluid communication with the conversion stage for cooling the mono-olefins from the conversion stream. The selective hydrogenation stage is upstream of the conversion stage and downstream of the fractionation stage.

BRIEF DESCRIPTION OF THE DRAWINGS

The present invention will hereinafter be described in conjunction with the following sole drawing figure, wherein like numerals denote like elements, and wherein.

DETAILED DESCRIPTION

Figure 1:
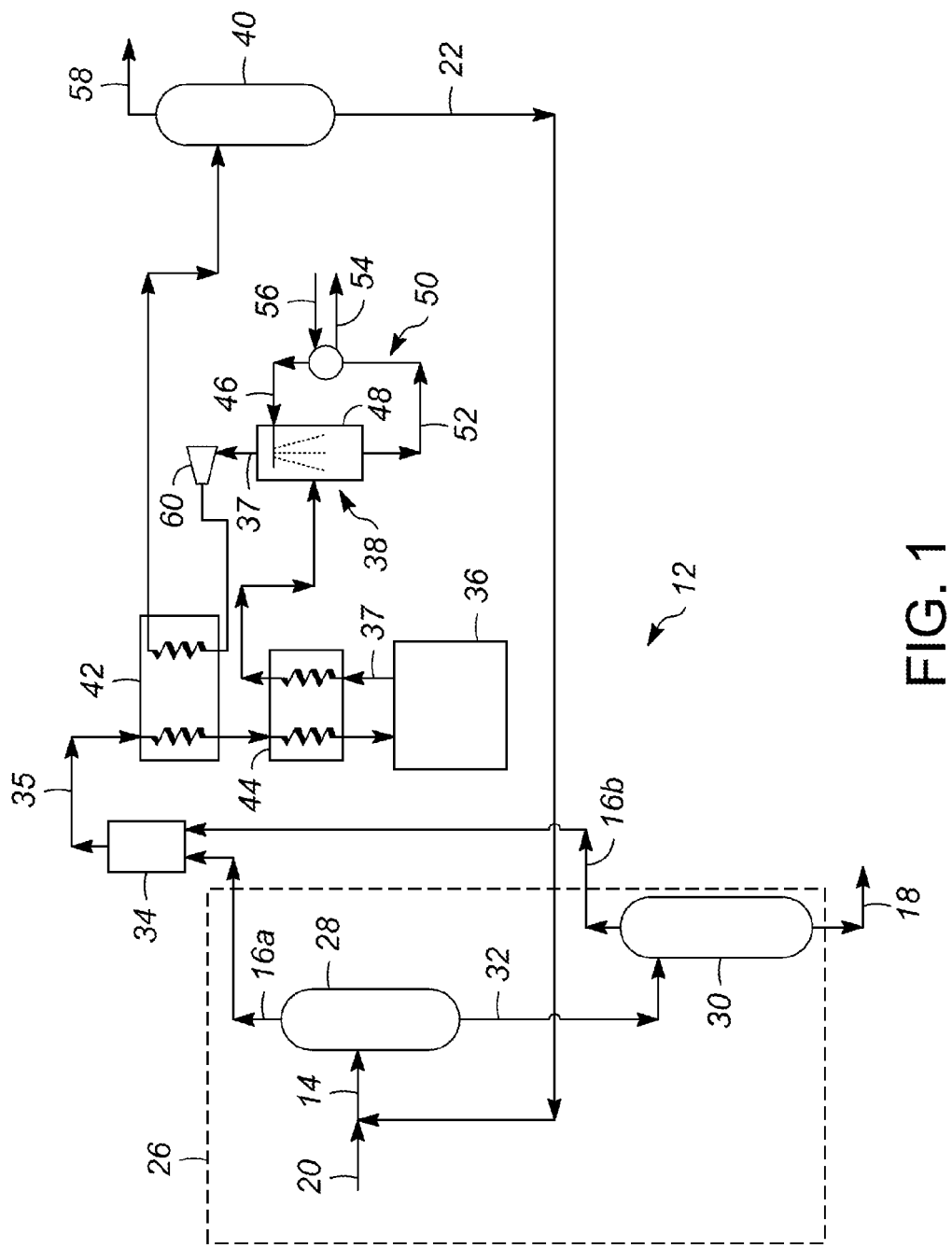
FIG. 1 is a schematic diagram of an exemplary embodiment of a hydrocarbon processing apparatus.

The following detailed description is merely exemplary in nature and is not intended to limit the invention or the application and uses of the invention. Furthermore, there is no intention to be bound by any theory presented in the preceding background or the following detailed description.

Processes and hydrocarbon processing apparatuses for preparing mono-olefins are provided herein. The processes and hydrocarbon processing apparatuses provided herein enable conversion of paraffins from a hydrocarbon feed into corresponding mono-olefins in a conversion stream and subsequent contact cooling of the mono-olefins from the conversion stream with an impurity-containing liquid hydrocarbon stream. Further, the processes and hydrocarbon processing apparatuses enable selective hydrogenation of dienes and/or acetylenes, in conjunction with the aforementioned contact cooling with the impurity-containing liquid hydrocarbon stream, regardless of the types of selective hydrogenation catalyst used. In particular, as described in further detail below, the processes and hydrocarbon processing apparatuses are configured such that dienes and/or acetylenes are selectively hydrogenated prior to converting the paraffins into mono-olefins and after separating a first fraction of carbon-containing compounds having less than or equal to 5 carbon atoms from the hydrocarbon feed. In this manner, any dienes and/or acetylenes that are present in the hydrocarbon feed, which may originate from fresh feed and/or recycle feed, are selectively hydrogenated prior to converting the paraffins from the hydrocarbon feed into corresponding mono-olefins, where the presence of dienes and/or acetylenes could result in high incidence of undesirable coke formation and accelerated spending of conversion catalyst, such as dehydrogenation catalysts. At the same time, the separated first fraction may be substantially free of impurities, such as sulfur-, mercury-, arsenic-, nitrogen-, and/or oxygen-containing compounds, as a result of separation of the first fraction from the hydrocarbon feed prior to selective hydrogenation, thereby substantially avoiding negative effects of any such impurities on selective hydrogenation catalysts. In this regard, recycle feed that may contain impurities introduced by contact cooling with the impurity-containing liquid hydrocarbon stream can be included in the hydrocarbon feed since the impurities are separated and substantially absent from the first fraction. Because contact cooling with the impurity-containing liquid hydrocarbon stream can be employed with marginal impact on selective hydrogenation catalysts used in the hydrocarbon processing apparatuses and processes described herein, conversion of the paraffins from the first fraction to corresponding mono-olefins in a conversion stream can be conducted at lower pressures than have been feasible with other cooling apparatuses, thereby enabling maximized paraffin to olefin conversion to be attained.

An exemplary embodiment of a hydrocarbon processing apparatus 12 for preparing mono-olefins is illustrated in FIG. 1. A process for preparing mono-olefins using the hydrocarbon processing apparatus 12 includes subjecting a hydrocarbon feed 14 to a fractionation stage 26. The hydrocarbon feed 14 refers to all sources of hydrocarbons that are subject to separation into one or more first fractions 16a and/or 16b and a second fraction 18 and may include fresh feed 20, i.e., feed that is provided from a source that is outside of the process, and/or a recycle feed 22, i.e., feed that is provided from a source within the process such as a paraffin-containing fraction 22 as described in further detail below. The fresh feed 20 may originate from other refining processes, and can be subject to adsorption to remove some impurities therefrom. In an embodiment, recycle feed 22 forms half to a majority of the hydrocarbon feed 14. For example, the recycle feed 22 may form from about 50 to about 80 weight percent (wt. %) of the hydrocarbon feed 14, based on the total weight of the hydrocarbon feed 14, with the balance of the hydrocarbon feed 14 being fresh feed 20. The hydrocarbon feed 14 at least contains a paraffin component. The paraffin component can include C1 to C12 paraffins, such as C2 to C5 paraffins or C2 to C4 paraffins. In addition to the paraffin component, the hydrocarbon feed 14 also includes other hydrocarbons such as, but not limited to, dienes, acetylenes, and combinations thereof and may further include mono-olefins. Additionally, impurities may also be present in the hydrocarbon feed 14, which may include sulfur-, mercury-, arsenic-, nitrogen-, and/or oxygen-containing compounds, with the impurities being separated from the first fraction 16a and/or 16b as described in further detail below.

As alluded to above, an exemplary process includes the step of separating the first fraction 16a and/or 16b of carbon-containing compounds having less than or equal to 5 carbon atoms from the hydrocarbon feed 14. In an embodiment, as shown in FIG. 1, the step of separating the first fraction 16a and/or 16b from the hydrocarbon feed 14 may be conducted in a fractionation stage 26 of an exemplary embodiment of the hydrocarbon processing apparatus 12. The fractionation stage 26 is configured to receive the hydrocarbon feed 14 and separate the hydrocarbon feed 14 into a plurality of fractions 16a and/or 16b, and 18, as described in further detail below. Fractionation techniques for separating compounds of different molecular weights are well known in the art. The fresh feed 20 and recycle feed 22 may be combined prior to introducing the hydrocarbon feed 14 into the fractionation stage 26, or may be separately fed to the fractionation stage 26 and combined therein. The hydrocarbon feed 14 is separated into the first fraction 16a and/or 16b of carbon-containing compounds having less than or equal to 5 carbon atoms and a second fraction 18 of compounds that have a lower vapor pressure than those in the first fraction 16a and/or 16b, such as carbon-containing compounds having greater than 5 carbon atoms and impurities such as sulfur-, mercury-, arsenic-, nitrogen-, and/or oxygen-containing compounds that have a lower vapor pressure than carbon-containing compounds having less than or equal to 5 carbon atoms. By separating the hydrocarbon feed 14 into the first fraction 16a and/or 16b of carbon-containing compounds having less than or equal to 5 carbon atoms and the second fraction 18 of compounds having a lower vapor pressure than those in the first fraction 16a and/or 16b, impurities such as sulfur-, mercury-, arsenic-, nitrogen-, and/or oxygen-containing compounds that have a lower vapor pressure than carbon-containing compounds having less than or equal to 5 carbon atoms can effectively be separated from the first fraction 16a and/or 16b. It is to be appreciated that, under some circumstances, impurities may be present in the hydrocarbon feed that have a higher vapor pressure than carbon-containing compounds having less than or equal to 5 carbon atoms. When it is desirable to remove such impurities, e.g., when such impurities may affect selective hydrogenation catalysts used in the process, the first fraction 16a and/or 16b may only include carbon-containing compounds, such as carbon-containing compounds having less than or equal to 3 carbon atoms, that have a higher vapor pressure than the subject impurities. In any event, the first fraction 16a and/or 16b generally only includes carbon-containing compounds that have a higher vapor pressure than the subject impurities whose presence during selective hydrogenation is undesirable.

As described in further detail below, dienes from the first fraction 16a and/or 16b are selectively hydrogenated, and paraffins from the first fraction 16a and/or 16b are converted into corresponding mono-olefins in a conversion stream 37. As such, as referred to herein, the first fraction 16a and/or 16b is any fraction or fractions including carbon-containing compounds having less than or equal to 5 carbon atoms that is subject to further processing through selective hydrogenation and conversion of paraffins. In this regard, the first fraction 16a and/or 16b may refer to multiple separate streams 16a, 16b that are individually processed through selective hydrogenation and conversion of paraffins, or may refer to a single stream 16a or 16b that is so processed. In any event, the first fraction 16a and/or 16b is substantially free of impurities present therein, with such impurities (as well as hydrocarbons having lower vapor pressures than compounds present in the first fraction 16a and/or 16b) present in the second fraction 18.

In an embodiment, the step of separating the hydrocarbon feed 14 includes a plurality of separation steps. In this embodiment, the first fractions 16a, 16b include a C3 fraction 16a and a C4 fraction 16b that are separated from the hydrocarbon feed 14 through the plurality of separation steps. Referring to FIG. 1, the fractionation stage 26 may include a plurality of fractionation columns 28, 30 that can be used to separate the hydrocarbon feed 14 in the plurality of separation steps. In this embodiment, the C3 fraction 16a and the C4 fraction 16b are separated from the hydrocarbon feed 14 by the plurality of fractionation columns 28, 30. In particular, the plurality of fractionation columns 28, 30 may include a depropanizer column 28 in series with a downstream debutanizer column 30. The depropanizer column 28 may receive the hydrocarbon feed 14 and separate the C3 fraction 16a therefrom, with a depropanizer bottom stream 32 from the depropanizer column 28 fed to the debutanizer column 30. The debutanizer column 30 may separate the C4 fraction 16b from the depropanizer bottom stream 32 that is introduced therein, with a debutanizer bottom stream 18 from the debutanizer column 30 representing the second fraction 18 that includes hydrocarbons and the impurities having a lower vapor pressure than compounds present in the first fraction 16a and/or 16b. In this regard, the second fraction 18 is separated from the C4 fraction after the C3 fraction is separated from the C4 fraction. Alternatively, although not shown, it is also to be appreciated that the hydrocarbon feed 14 can be separated into additional fractions beyond a C3 fraction 16a and a C4 fraction 16b. For example, a C5 fraction (not shown) can also be separated after separating the C4 fraction 16b from the hydrocarbon feed 14, with the second fraction 18 being separated from the C5 fraction instead of the C4 fraction 16b. In this embodiment, a depentanizer column (not shown) for separating a C5 fraction could also be included in series with the depropanizer column 28 and debutanizer column 30, with the second fraction 18 separated from the C5 fraction. As another alternative, it is also to be appreciated that a single fractionation column (not shown) could be used, with the C3 fraction 16a, C4 fraction 16b, C5 fraction, and second fraction 18 being withdrawn at different levels within the single fractionation column.

Next, dienes and/or acetylenes from the first fraction 16a and/or 16b are selectively hydrogenated into corresponding mono-olefins, prior to converting the paraffins from the first fraction 16a and/or 16b into mono-olefins and after separating the first fraction 16a and/or 16b from the hydrocarbon feed 14. Selective hydrogenation of dienes and/or acetylenes is known in the art and a variety of techniques are known for selectively hydrogenating dienes and/or acetylenes. Selective hydrogenation techniques include, for example, the Hüls Selective Hydrogenation Process (SHP), in which hydrogenation of the dienes and/or acetylenes is carried out at mild conditions with a slight stoichiometric excess of hydrogen in the presence of a selective hydrogenation catalyst. Suitable selective hydrogenation catalysts include, but are not limited to, those containing noble metals such as palladium. As set forth above, the processes and hydrocarbon processing apparatuses 12 described herein enable selective hydrogenation of dienes and/or acetylenes regardless of the types of selective hydrogenation catalyst used due to the separation of the impurities from the first fraction 16a and/or 16b, which impurities may otherwise control the types of selective hydrogenation catalysts that could be used.

As set forth above, selective hydrogenation of the dienes and/or acetylenes is beneficial, prior to conversion of paraffins in the first fraction 16a and/or 16b into corresponding mono-olefins, because the presence of dienes and/or acetylenes could result in high incidence of undesirable coke formation and accelerated spending of conversion catalyst, such as dehydrogenation catalysts. By selectively hydrogenating the dienes and/or acetylenes prior to converting the paraffins from the first fraction 16a and/or 16b into mono-olefins, coke formation on the conversion catalyst can be minimized Further, because impurities that could impact selective hydrogenation catalysts are substantially absent from the first fraction 16a and/or 16b, negative effects of any such impurities on selective hydrogenation catalysts are effectively avoided.

Although the dienes and/or acetylenes are selectively hydrogenated, other hydrocarbons present in the first fraction 16a and/or 16b after separating the hydrocarbon feed 14 may also present during selective hydrogenation of the dienes and/or acetylenes, although such other hydrocarbons (including mono-olefins and paraffins) are generally unaffected by the selective hydrogenation techniques. In an embodiment, the first fraction 16a and/or 16b is directly subject to selective hydrogenation, although it is to be appreciated that the first fraction 16a and/or 16b may be subject to intermediate processing steps between the step of separating the first fraction 16a and/or 16b and the step of selectively hydrogenating the dienes and/or acetylenes from the first fraction 16a and/or 16b. In embodiments in which the first fractions 16a and 16b include the C3 fraction 16a and the C4 fraction 16b, the dienes and/or acetylenes in the respective fractions can each be separately selectively hydrogenated.

Referring to FIG. 1, an exemplary embodiment of the hydrocarbon processing apparatus 12 includes a selective hydrogenation stage 34 in fluid communication with the fractionation stage 26 for receiving a fraction from the fractionation stage 26 and selectively hydrogenating dienes and/or acetylenes in the fraction into corresponding mono-olefins of an effluent 35. The selective hydrogenation stage 34 is upstream of a conversion stage 36, as described in further detail below, and downstream of the fractionation stage 26. The process in accordance with an embodiment includes selectively hydrogenating dienes and/or acetylenes from the first fraction 16a and/or 16b into corresponding mono-olefins in the selective hydrogenation stage 34 of the hydrocarbon processing apparatus 12. The dienes and/or acetylenes from the first fraction 16a and/or 16b are selectively hydrogenated prior to converting the paraffins from the first fraction 16a and/or 16b into mono-olefins, as described in further detail below, and after separating the first fraction 16a and/or 16b from the hydrocarbon feed 14. When the hydrocarbon processing apparatus 12 includes the plurality of fractionation columns 28, 30, as shown in FIG. 1, the individual fractionation columns 28, 30 may be separately connected to distinct selective hydrogenation stages (although only a single selective hydrogenation stage 34 is shown), thereby enabling separate processing of the C3 fraction 16a and the C4 fraction 16b.

After selective hydrogenation, paraffins from the first fraction 16a and/or 16b are converted into corresponding mono-olefins in a conversion stream 37. An exemplary embodiment of the hydrocarbon processing apparatus 12 includes a conversion stage 36 in fluid communication with the selective hydrogenation stage 34 for receiving effluent 35 from the selective hydrogenation stage 34 and for converting paraffins in the effluent 35 into corresponding mono-olefins in a conversion stream 37. In this embodiment, paraffins are converted from the first fraction 16a and/or 16b into corresponding mono-olefins in the conversion stage 36 of the hydrocarbon processing apparatus 12, with the mono-olefins being present in the conversion stream 37 that exits the conversion stage 36. As shown in the embodiment of the hydrocarbon processing apparatus 12 of FIG. 1, it is to be appreciated that conversion of the paraffins from the first fraction 16a and/or 16b into corresponding mono-olefins can be conducted separately for the C3 fraction 16a and the C4 fraction 16b when the first fraction 16a and 16b includes those fractions separate from each other. Although FIG. 1 only shows one selective hydrogenation stage 34 and conversion stage 36, with paraffins from the C3 fraction 16a and the C4 fraction 16b converted to corresponding mono-olefins in a common conversion stage 36, it is to be appreciated that dedicated selective hydrogenation stages and conversion stages (not shown) can be provided for the respective first fractions 16a, 16b.

Various techniques are known for converting paraffins into corresponding mono-olefins including, but not limited to, steam cracking, dehydrogenation of C3-C5 paraffins, fluid catalytic cracking, and the like. In an embodiment, the paraffins from the first fraction 16a and/or 16b are converted to mono-olefins through dehydrogenation, which generally involves heating the paraffins under catalysis conditions in the presence of a dehydrogenation catalyst as the conversion catalyst. One example of a suitable dehydrogenation technique is known in the art as the UOP Pacol Dehydrogenation Process. In this embodiment, the conversion stage 36 of the hydrocarbon processing apparatus 12 is further defined as a dehydrogenation stage 36 in which paraffins from the first fraction 16a and/or 16b are converted to mono-olefins through dehydrogenation. Suitable dehydrogenation catalysts and reaction temperature ranges are generally known in the art based upon the particular distribution of paraffins to be converted (i.e., for the C3 fraction 16a and C4 fraction 16b). Like with selective hydrogenation and as shown in FIG. 1, when the first fractions 16a and 16b include the separate C3 fraction 16a and C4 fraction 16b, the paraffins in the respective fractions 16a, 16b may be separately converted into corresponding mono-olefins in separate conversion steps that are dedicated to the respective fractions 16a, 16b.

Conversion of paraffins into corresponding mono-olefins is most efficient at minimized pressures due to favorable dehydrogenation equilibriums at lower pressures. In accordance with the embodiment in which the paraffins from the first fraction 16a and/or 16b are converted to corresponding mono-olefins through dehydrogenation, the paraffins may be dehydrogenated at a pressure of less than or equal to about 27.5 kilopascals (kPa), such as from about 20 to 27.5 kPa, thereby enabling maximized paraffin to olefin conversion to be attained. Such low pressures are possible in view of the use of contact cooling, as described in further detail below.

By-products of dehydrogenation of the paraffins from the first fraction 16a and/or 16b include dienes and/or acetylenes. The dienes and/or acetylenes are included, for example, in the conversion stream 37 along with unreacted paraffins and the mono-olefins after conversion. As described in further detail below, the conversion stream 37 may be separated into a mono-olefin fraction 58 and a paraffin-containing fraction 22, which includes the dienes and/or acetylenes along with unreacted paraffins. The paraffin-containing fraction 22 may then be recycled back as part of the hydrocarbon feed 14.

In an embodiment, effluent 35 produced from selectively hydrogenating the dienes and/or acetylenes from the first fraction 16a and/or 16b is subject to conversion of paraffins therein into mono-olefins. In this regard, the effluent 35 from selectively hydrogenating the dienes and/or acetylenes may be directly converted without adding or removing any components from the effluent 35. The effluent 35 may be subject to one or more heat exchange steps to increase the temperature thereof prior to dehydrogenation, and such heat exchange steps may be conducted between the selective hydrogenation stage 34 and the conversion stage 36. For example, as shown in FIG. 1, the exemplary embodiment of the hydrocarbon processing apparatus 12 includes an optional cold box 42 and an optional additional heat exchanger 44 in series between the selective hydrogenation stage 34 and the conversion stage 36. In this embodiment, effluent 35 from the selective hydrogenation stage 34 may first be directed through the cold box 42, where heat is extracted from the conversion stream 37 that includes the mono-olefins after the conversion stream 37 has undergone prior cooling steps described in further detail below. The effluent 35 may then pass through the additional heat exchanger 44 that transfers heat from the conversion stream 37 to the effluent 35 from the selective hydrogenation stage 34 immediately after conversion of the paraffins in the conversion stage 36, after which the effluent 35 is fed to the conversion stage 36. The conversion stream 37 is in vapor form when passed through the additional heat exchanger 44 and may be in liquid form when passed through the cold box 42, as described in further detail below.

From the conversion stage 36, the mono-olefins from the conversion stream 37 are contact cooled with an impurity-containing liquid hydrocarbon stream 46 in a contact cooling stage 38, in preparation for separating the converted mono-olefins from the conversion stream 37. The impurity-containing liquid hydrocarbon stream 46 may be any hydrocarbon stream that is in liquid form for cooling the conversion stream 37, and may include impurities that have a lower vapor pressure than compounds in the first fraction 16a and/or 16b, which may include sulfur-, mercury-, arsenic-, nitrogen-, and/or oxygen-containing compounds. The impurities may even affect selective hydrogenation catalysts that are employed during selective hydrogenation of the first fraction 16a and/or 16b. Due to abundant availability in certain processing plants, the impurity-containing liquid hydrocarbon stream 46 may be further defined as light cycle oil 46 that includes sulfur-containing impurities such as, but not limited to, hydrogen sulfide and carbonyl sulfide. The presence of impurities in the impurity-containing liquid hydrocarbon stream 46 is immaterial because, to the extent that impurities from the impurity-containing liquid hydrocarbon stream 46 are transferred to the conversion stream 37 during contact cooling, selective hydrogenation of the conversion stream 37 is unnecessary and the conversion stream 37 does not undergo further reactions prior to separating the converted mono-olefins from the conversion stream 37. As such, because the impurities have a lower vapor pressure than compounds that are in the first fraction 16a and/or 16b, any such impurities that are present in the conversion stream 37 after contact cooling may be substantially removed from recycled fractions 22 of the conversion stream 37 during separation of the first fraction 16a and/or 16b from the hydrocarbon feed 14.

As shown in FIG. 1, the contact cooling stage 38 may include one or more cooling columns 48 that facilitate direct contact between the conversion stream 37 and the impurity-containing liquid hydrocarbon stream 46. The conversion stream 37 may be in vapor form before and after contact cooling and, because the impurity-containing liquid hydrocarbon stream 46 is in liquid form, there is little loss of components from the conversion stream 37 to the impurity-containing liquid hydrocarbon stream 46 under such circumstances. The contact cooling stage 38 may also include a recycle system 50 that recycles a portion of a liquid bottom stream 52 from the cooling column 48. A portion 54 of the liquid bottom stream 52 is removed from the contact cooling stage 38 and can be used in other processes. Fresh impurity-containing hydrocarbons 56 are combined with the recycled portion of the liquid bottom stream 52 and returned to the cooling column 48 as the impurity-containing liquid hydrocarbon stream 46.

As alluded to above, and as shown in FIG. 1, an embodiment of the hydrocarbon processing apparatus 12 may include the cold box 42 and the additional heat exchanger 44, in addition to the contact cooling stage 38. In this embodiment, the conversion stream 37 is fed from the conversion stage 36 to the additional heat exchanger 44, where heat is exchanged between the conversion stream 37 (which is in vapor form) and the effluent 35 from the selective hydrogenation stage 34 (which is in liquid form). Also in this embodiment, from the additional heat exchanger 44, the conversion stream 37 is fed to the contact cooling stage 38. The conversion stream 37, after passing through the contact cooling stage 38, is still in vapor form and may subsequently be condensed in an optional condenser 60. The condensed conversion stream 37 is fed to the cold box 42, where the condensed conversion stream 37 is further cooled through heat transfer with the effluent 35 from the selective hydrogenation stage 34. The condensed conversion stream 37 may be subject to treatment steps (not shown), such as adsorption, prior to feeding into the cold box 42.

The process continues by separating the conversion stream 37 into a mono-olefin fraction 58 and the paraffin-containing fraction 22. Separation of the conversion stream 37, like separation of the initial hydrocarbon feed 14, may include a plurality of separation steps in which fractions having progressively lower vapor pressures are separated from the conversion stream 37. Techniques for separating mono-olefins from a conversion stream that contains mono-olefins and unreacted paraffins are known in the art. Referring to FIG. 1, an exemplary embodiment of the hydrocarbon processing apparatus 12 may include a mono-olefin separation stage 40 in fluid communication with the contact cooling stage 38 for receiving the conversion stream 37 produced by dehydrogenation and for separating the conversion stream 37 into the mono-olefin fraction 58 and the paraffin-containing fraction 22. In the embodiment of FIG. 1, the conversion stream 37 can be separated into the mono-olefin fraction 58 and the paraffin-containing fraction 22 in the mono-olefin separation stage 40 after contact cooling the converted mono-olefins in the conversion stream 37. As set forth above, the paraffin-containing fraction 22 may include impurities from the impurity-containing liquid hydrocarbon stream 46 that is employed in contact cooling. As also shown in FIG. 1, the paraffin-containing fraction 22 may be recycled to the hydrocarbon feed 14 or the fractionation stage 26, although it is to be appreciated that recycling is optional. In particular, in this embodiment, the mono-olefin separation stage 40, in addition to being in fluid communication with the contact cooling stage 38, is further in fluid communication with the fractionation stage 26 for recycling the paraffin-containing fraction 22 to the fractionation stage 26. It is to be appreciated that, in an embodiment of the hydrocarbon processing apparatus 12 as shown in FIG. 1, the optional cold box 42 and optional condenser 60 can be disposed between the contact cooling stage 38 and the mono-olefin separation stage 40. As set forth above, the impurities from the paraffin-containing fraction 22 may be separated from the hydrocarbon feed 14 into the second fraction 18 in the fractionation stage 26.

The paraffin-containing fraction 22 that is separated from the conversion stream 37 refers to any fraction separated from the conversion stream 37 that is intended to contain predominantly paraffins (although it is to be appreciated that trace paraffins may be contained in the mono-olefin fraction). As such, when the plurality of separation steps are employed, any fractions that are intended to predominantly contain mono-olefins are considered part of the mono-olefin fraction 58, and any fractions that are intended to contain predominantly paraffins are considered part of the paraffin-containing fraction 22. The paraffin-containing fraction 22 includes impurities from the impurity-containing liquid hydrocarbon stream 46 that is employed in contact cooling, and also includes dienes and/or acetylenes that result from conversion of paraffins into mono-olefins. The paraffin-containing fraction 22 may be recycled to the hydrocarbon feed 14 or the fractionation stage 26, where the impurities from the paraffin-containing fraction 22 are separated from the hydrocarbon feed 14 into the second fraction 18. In this manner, impurities that may affect selective hydrogenation catalysts can be removed from the process prior to selective hydrogenation of dienes and/or acetylenes from the first fraction 16a and/or 16b. Further, dienes and/or acetylenes that result from conversion of paraffins into mono-olefins can also be recycled within the process and selectively hydrogenated to yield additional mono-olefins.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention. It being understood that various changes may be made in the function and arrangement of elements described in an exemplary embodiment without departing from the scope of the invention as set forth in the appended claims.

What is claimed is:

1. A process for preparing mono-olefins in a hydrocarbon processing apparatus, said method comprising the steps of:

separating a hydrocarbon feed into a first fraction of carbon-containing compounds having less than or equal to 5 carbon atoms and a second fraction containing compounds having a lower vapor pressure than those in the first fraction in a fractionation stage of the hydrocarbon processing apparatus;

selectively hydrogenating dienes and/or acetylenes from the first fraction into corresponding mono-olefins in a selective hydrogenation stage of the hydrocarbon processing apparatus to form a selective hydrogenation stream;

dehydrogenating paraffins contained in the selective hydrogenation stream into corresponding mono-olefins to form a dehydrogenation stream within a conversion stage of the hydrocarbon processing apparatus;

contact cooling the dehydrogenation stream with an impurity-containing liquid hydrocarbon stream in a contact cooling stage of the hydrocarbon processing apparatus to form a cooled dehydrogenation stream containing impurities having a lower vapor pressure than compounds in the first fraction, wherein the impurities include sulfur-, mercury-, arsenic-, nitrogen-, and/or oxygen-containing compounds;

separating the cooled dehydrogenation stream into a mono-olefin fraction and a paraffin-containing fraction in a mono-olefin separation stage, wherein the paraffin-containing fraction comprises said impurities and wherein the paraffin-containing fraction is recycled to the step of separating the hydrocarbon feed in the fractionation stage;

wherein the dienes and/or acetylenes from the first fraction are selectively hydrogenated prior to converting the paraffins from the first fraction into mono-olefins and after separating the first fraction from the hydrocarbon feed.

2. The process of claim 1, wherein the fractionation stage comprises a plurality of fractionation columns, and wherein the first fraction comprises a C3 fraction and a C4 fraction.

3. The process of claim 2, wherein the C3 fraction is separated from the C4 fraction and the second fraction is separated from the C4 fraction after separation of the C3 fraction from the C4 fraction.

4. The process of claim 2, wherein paraffins from the C3 fraction and the C4 fraction are separately dehydrogenated into corresponding mono-olefins in separate dehydrogenation streams.

5. The process of claim 2, wherein paraffins from the C3 fraction and the C4 fraction are dehydrogenated to corresponding mono-olefins in a common dehydrogenation stage.

6. The process of claim 1, the paraffins are dehydrogenated at a pressure of less than or equal to about 27.5 kilopascals.

7. The process of claim 1, wherein the impurity-containing liquid hydrocarbon stream is a light cycle oil comprising sulfur-containing compounds.

8. The process of claim 1, wherein the impurities from the paraffin-containing fraction are separated from the hydrocarbon feed into the second fraction in the fractionation stage.

* * * * *